United States Patent [19]
Pineiro et al.

[11] Patent Number: 5,837,715
[45] Date of Patent: Nov. 17, 1998

[54] 3-FLUORO-4-AMINOPIPERIDINE DERIVATIVES AS 5-HT RECEPTOR AGONISTS

[75] Inventors: J. L. Castro Pineiro; M. G. Russell, both of Hertfordshire, England

[73] Assignee: Merck Sharp & Dohme Ltd., Hoddesdon, England

[21] Appl. No.: 896,559

[22] Filed: Jul. 17, 1997

[51] Int. Cl.$^6$ .................. A61K 31/445; C07D 401/14
[52] U.S. Cl. ............................................. 514/323
[58] Field of Search ................................ 544/129, 233, 544/238, 360; 546/113, 193, 156, 201, 202, 207, 208, 209, 210, 212; 514/235.2, 236.5, 255, 256, 300, 301, 302, 303, 318, 323, 326

[56] References Cited

U.S. PATENT DOCUMENTS

| | | | |
|---|---|---|---|
| 5,576,336 | 11/1996 | Baker et al. | 514/323 |
| 5,637,593 | 6/1997 | Porter et al. | 514/274 |
| 5,708,008 | 1/1998 | Audia | 514/323 |

FOREIGN PATENT DOCUMENTS

| | | |
|---|---|---|
| WO 95/32196 | 11/1995 | WIPO . |
| WO 96/04269 | 2/1996 | WIPO . |
| WO 96/04274 | 2/1996 | WIPO . |
| WO 96/16056 | 5/1996 | WIPO . |
| WO 96/17842 | 6/1996 | WIPO . |
| 97/18202 | 5/1997 | WIPO . |
| 98/06725 | 2/1998 | WIPO . |

*Primary Examiner*—Ceila Chang
*Attorney, Agent, or Firm*—Philippe L. Durette; Melvin Winokur

[57] ABSTRACT

A class of substituted 3-fluoro-4-aminopiperidine derivatives are selective agonists of 5-HT$_1$-like receptors, being potent agonists of the human 5-HT$_{1D_\alpha}$ receptor subtype whilst possessing at least a 10-fold selective affinity for the 5-HT$_{1D_\alpha}$ receptor subtype relative to the 5-HT$_{1D_\beta}$ subtype; they are therefore useful in the treatment and/or prevention of clinical conditions, in particular migraine and associated disorders, for which a subtype-selective agonist of 5-HT$_{1D}$ receptors is indicated, while eliciting fewer side-effects, notably adverse cardiovascular events, than those associated with non-subtype-selective 5-HT$_{1D}$ receptor agonists.

18 Claims, No Drawings

3-FLUORO-4-AMINOPIPERIDINE DERIVATIVES AS 5-HT RECEPTOR AGONISTS

The present invention relates to a class of substituted 3-fluoro-4-aminopiperidine derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

It has been known for some time that 5-HT$_1$-like receptor agonists which exhibit selective vasoconstrictor activity are of use in the treatment of migraine (see, for example, A. Doenicke et al., *The Lancet*, 1988, Vol. 1, 1309–11; and W. Feniuk and P. P. A. Humphrey, *Drug Development Research*, 1992, 26, 235–240).

The human 5-HT$_1$-like or 5-HT$_{1D}$ receptor has recently been shown by molecular cloning techniques to exist in two distinct subtypes. These subtypes have been termed 5-HT$_{1D_\alpha}$ (or 5-HT$_{1D\text{-}1}$) and 5-HT$_{1D_\beta}$ (or 5-HT$_{1D\text{-}2}$), and their amino acid sequences are disclosed and claimed in WO-A-91/17174.

The 5-HT$_{1D_\alpha}$ receptor subtype in humans is believed to reside on sensory terminals in the dura mater. Stimulation of the 5-HT$_{1D_\alpha}$ a subtype inhibits the release of inflammatory neuropeptides which are thought to contribute to the headache pain of migraine. The human 5-HT$_{1D_\beta}$ receptor subtype, meanwhile, is located predominantly on the blood vessels and in the brain, and hence may play a part in mediating constriction of cerebral and coronary arteries, as well as CNS effects.

Administration of the prototypical 5-HT$_{1D}$ agonist sumatriptan (GR43175) to humans is known to give rise at therapeutic doses to certain adverse cardiovascular events (see, for example, F. Willett et al., *Br. Med. J.,* 1992, 304, 1415; J. P. Ottervanger et al., *The Lancet,* 1993, 341, 861–2; and D. N. Bateman, *The Lancet,* 1993, 341, 221–4). Since sumatriptan barely discriminates between the human 5-HT$_{1D_\alpha}$ and 5-HT$_{1D_\beta}$ receptor subtypes (cf. WO-A-91/17174, Table 1), and since it is the blood vessels with which the 5-HT$_{1D_\beta}$ subtype is most closely associated, it is believed that the cardiovascular side-effects observed with sumatriptan can be attributed to stimulation of the 5-HT$_{1D_\beta}$ receptor subtype. It is accordingly considered (cf. G. W. Rebeck et al., *Proc. Natl. Acad. Sci. USA,* 1994, 91, 3666–9) that compounds which can interact selectively with the 5-HT$_{1D_\alpha}$ receptor subtype, whilst having a less pronounced action at the 5-HT$_{1D_\beta}$ subtype, might be free from, or at any rate less prone to, the undesirable cardiovascular and other side-effects associated with non-subtype-selective 5-HT$_{1D}$ receptor agonists, whilst at the same time maintaining a beneficial level of anti-migraine activity.

The compounds of the present invention, being selective 5-HT$_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human 5-HT$_{1D_\alpha}$ receptor subtype. Moreover, the compounds in accordance with this invention have been found to possess at least a 10-fold selective affinity for the 5-HT$_{1D_\alpha}$ receptor subtype relative to the 5-HT$_{1D_\beta}$ subtype, and they can therefore be expected to manifest fewer side-effects than those associated with non-subtype-selective 5-HT$_{1D}$ receptor agonists.

Several distinct classes of substituted five-membered heteroaromatic compounds are described in published European patent applications 0438230, 0494774 and 0497512, and published International patent applications 93/18029, 94/02477 and 94/03446. The compounds described therein are stated to be agonists of 5-HT$_1$-like receptors, and accordingly to be of particular use in the treatment of migraine and associated conditions. None of these publications, however, discloses nor even suggests the substituted 3-fluoro-4-aminopiperidine derivatives provided by the present invention.

WO-A-94/08993 and WO-A-95/28400 describe substituted pyridinyl-benzofuran derivatives, and analogues thereof. These compounds are stated therein to be selective agonists at 5-HT$_1$-like receptors and thus useful in treating conditions associated with cephalic pain, including migraine. Neither of these publications, however, discloses or even suggests the substituted 3-fluoro-4-aminopiperidine derivatives provided by the present invention.

In EP-A-0548813 is described a series of alkoxypyridin-4-yl and alkoxypyrimidin-4-yl derivatives of indol-3-ylalkylpiperazines which are alleged to provide treatment of vascular or vascular-related headaches, including migraine. There is, however, no disclosure nor any suggestion in EP-A-0548813 of replacing the substituted piperazine moiety with a differently substituted piperidine moiety.

WO-A-91/18897 describes a class of tryptamine derivatives substituted by various five-membered rings, which are stated to be specific to a particular type of "5-HT$_1$-like" receptor and thus to be effective agents for the treatment of clinical conditions, particularly migraine, requiring this activity. A further class of tryptamine derivatives with alleged anti-migraine activity is disclosed in WO-A-94/02460. However, neither WO-A-91/18897 nor WO-A-94/02460 discloses or suggests the substituted 3-fluoro-4-aminopiperidine derivatives provided by the present invention.

Moreover, nowhere in the prior art mentioned above is there any disclosure of a subtype-selective 5-HT$_{1D}$ receptor agonist having a 5-HT$_{1D_\alpha}$ receptor binding affinity (IC$_{50}$) below 50 nM and at least a 10-fold selective affinity for the 5-HT$_{1D_\alpha}$ receptor subtype relative to the 5-HT$_{1D_\beta}$ subtype.

WO-A-95/32196, WO-A-96/04269, WO-A-96/04274 and WO-A-96/16056 describe various classes of heterocyclic compounds as alpha subtype-selective agonists of the human 5-HT$_{1D}$ receptor. However, there is no disclosure nor any suggestion in any of these publications of the substituted 3-fluoro-4-aminopiperidine derivatives provided by the present invention.

The compounds according to the present invention are subtype-selective 5-HT$_{1D}$ receptor agonists having a human 5-HT$_{1D_\alpha}$ receptor binding affinity (IC$_{50}$) below 50 nM, typically below 10 nM and preferably below 1 nM; and at least a 10-fold selective affinity, typically at least a 20-fold selective affinity, suitably at least a 50-fold selective affinity and preferably at least a 100-fold selective affinity, for the human 5-HT$_{1D_\alpha}$ receptor subtype relative to the 5-HT$_{1D_\beta}$ subtype. Moreover, the compounds in accordance with this invention possess interesting properties in terms of their efficacy and/or bioavailability.

The present invention provides a compound of formula I, or a salt or prodrug thereof:

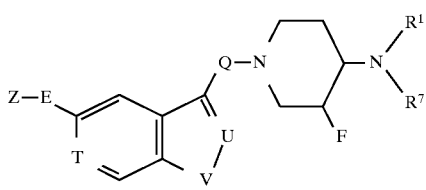

wherein

Z represents hydrogen, halogen, cyano, nitro, trifluoromethyl, —$OR^5$, —$OCOR^5$, —$OCONR^5R^6$, —$OCH_2CN$, —$OCH_2CONR^5R^6$, —$SR^5$, —$SOR^5$, —$SO_2R^5$, —$SO_2NR^5R^6$, —$NR^5R^6$, —$NR^5COR^6$, —$NR^5CO_2R^6$, —$NR^5SO_2R^6$, —$COR^5$, —$CO_2R^5$, —$CONR^5R^6$, or a group of formula (Za), (Zb), (Zc) or (Zd):

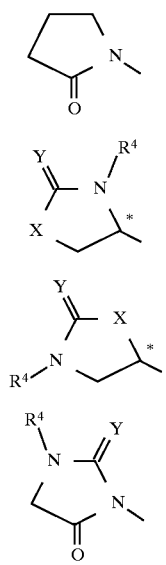

in which the asterisk * denotes a chiral centre; or

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole; or Z represents an optionally substituted six-membered heteroaromatic ring selected from pyridine, pyrazine, pyrimidine and pyridazine;

X represents oxygen, sulphur, —NH— or methylene;

Y represents oxygen or sulphur;

E represents a chemical bond or a straight or branched alkylene chain containing from 1 to 4 carbon atoms;

Q represents a straight or branched alkylene chain containing from 1 to 6 carbon atoms, optionally substituted in any position by one or more substituents selected from fluoro and hydroxy;

T represents nitrogen or CH;

U represents nitrogen or C—$R^2$;

V represents oxygen, sulphur or N—$R^3$;

$R^1$ represents aryl($C_{1-6}$)alkyl or heteroaryl($C_{1-6}$)alkyl, either of which groups may be optionally substituted;

$R^2$, $R^3$, $R^4$ and $R^7$ independently represent hydrogen or $C_{1-6}$ alkyl; and $R^5$ and $R^6$ independently represent hydrogen, $C_{1-6}$ alkyl, trifluoromethyl, phenyl, methylphenyl, or an optionally substituted aryl($C_{1-6}$)alkyl or heteroaryl($C_{1-6}$)alkyl group; or $R^5$ and $R^6$, when linked through a nitrogen atom, together represent the residue of an optionally substituted azetidine, pyrrolidine, piperidine, morpholine or piperazine ring.

Where Z in the compounds of formula I above represents a five-membered heteroaromatic ring, this ring may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z. Examples of suitable substituents on the five-membered heteroaromatic ring as specified for Z include $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano and trifluoromethyl.

Where Z in the compounds of formula I above represents a six-membered heteroaromatic ring, this ring may be optionally substituted by one or more substituents, typically by one or two substituents. Examples of suitable substituents on the six-membered heteroaromatic ring as specified for Z include $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, halogen, halo($C_{1-6}$)alkyl, cyano, cyano($C_{1-6}$)alkyl, trifluoromethyl, and —$(CH_2)_a$—$R^8$, in which a is zero, 1, 2 or 3 (preferably zero or 1) and $R^8$ represents —$OR^a$, —$OCOR^c$, —$OCO_2R^a$, —$SR^a$, —$SOR^a$, —$SO_2R^c$, —$CH=CHSO_2R^c$, —$SO_2NR^aR^b$, —$CH=CHSO_2NR^aR^b$, —$NR^aR^b$, —$NR^aCOR^c$, —$NR^aCO(CH_2)_bOR^d$ (in which b is 1 or 2, preferably 1), —$NR^aCO_2R^d$, —$NR^aSO_2R^c$, —$NR^dCONR^aR^b$, —$NR^dSO_2NR^aR^b$, —$COR^c$, —$CH=CHCOR^c$, —$CO_2R^a$, —$CONR^aR^b$, —$CH=CHCONR^aR^b$, or —$CONR^dNR^aR^b$, or $R^8$ represents a group of formula (a), (b), (c), (d) or (e):

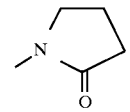

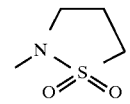

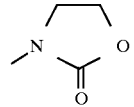

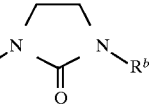

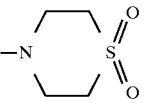

wherein $R^a$ and $R^d$ independently represent hydrogen, $C_{1-6}$ alkyl, trifluoromethyl, phenyl, fluorophenyl or tetrahydropyranyl; $R^b$ represents hydrogen, $C_{1-6}$ alkyl, trifluoromethyl, phenyl or fluorophenyl; and $R^c$ represents hydrogen, $C_{1-6}$ alkyl, trifluoromethyl, phenyl, fluorophenyl, tetrahydropyranyl, azetidinyl, pyrrolidinyl, piperidinyl or morpholinyl.

The group $R^1$ may be optionally substituted by one or more substituents, as also may the groups $R^5$ or $R^6$ where these represent aryl($C_{1-6}$)alkyl or heteroaryl($C_{1-6}$)alkyl. Where $R^1$, $R^5$ or $R^6$ represents aryl($C^{1-6}$)alkyl or heteroaryl ($C_{1-6}$)alkyl, any optional substitution will suitably be on the aryl or heteroaryl moiety thereof, although substitution on the alkyl moiety thereof is an alternative possibility. Examples of optional substituents thereon include halogen, cyano, trifluoromethyl, triazolyl, tetrazolyl, $C_{1-6}$ alkyl-tetrazolyl, hydroxy, keto, $C_{1-6}$ alkoxy, $C_{1-6}$ alkylthio, $C_{2-6}$ alkoxycarbonyl, $C_{2-6}$ alkylcarbonyl, $C_{1-6}$ alkylsulphonyl, arylsulphonyl, amino, $C_{1-6}$ alkylamino, di($C_{1-6}$)alkylamino, di($C_{1-6}$)alkylaminomethyl, $C_{2-6}$ alkylcarbonylamino, arylcarbonylamino, $C_{2-6}$ alkoxycarbonylamino, N-($C_{1-6}$) alkyl-N-($C_{2-6}$)alkoxycarbonylamino, $C_{1-6}$ alkylsulphonylamino, arylsulphonylamino, $C_{1-6}$ alkylsulphonylaminomethyl, aminocarbonylamino, $C_{1-6}$ alkylaminocarbonylamino, di($C_{1-6}$) alkylaminocarbonylamino, mono- or diarylaminocarbonylamino, pyrrolidinylcarbonylamino, piperidinylcarbonylamino, aminocarbonyl, $C_{1-6}$ alkylaminocarbonyl, di($C_{1-6}$)alkylaminocarbonyl, aminosulphonyl, $C_{1-6}$ alkylaminosulphonyl, di($C_{1-6}$) alkylaminosulphonyl, aminosulphonylmethyl, $C_{1-6}$ alkylaminosulphonylmethyl and di($C_{1-6}$) alkylaminosulphonylmethyl.

When $R^5$ and $R^6$, when linked through a nitrogen atom, together represent the residue of an azetidine, pyrrolidine, piperidine, morpholine or piperazine ring, this ring may be unsubstituted or substituted by one or more substituents. Examples of suitable substituents include $C_{1-6}$ alkyl, aryl ($C_{1-6}$)alkyl, $C_{1-6}$ alkoxy, $C_{2-6}$ alkoxycarbonyl and $C_{1-6}$ alkylaminocarbonyl. Typical substituents include methyl, benzyl, methoxy, methoxycarbonyl, ethoxycarbonyl and methylaminocarbonyl. In particular, where $R^5$ and $R^6$ together represent the residue of a piperazine ring, this ring is preferably substituted on the distal nitrogen atom by a $C_{2-6}$ alkoxycarbonyl moiety such as methoxycarbonyl or ethoxycarbonyl.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-6}$ alkoxy", "$C_{1-6}$ alkylthio" and "$C_{1-6}$ alkylamino" are to be construed accordingly.

The expression "$C_{2-6}$ alkenyl" as used herein refers to straight-chained and branched alkenyl groups containing from 2 to 6 carbon atoms. Typical examples include vinyl, allyl, dimethylallyl and butenyl groups.

The expression "$C_{2-6}$ alkynyl" as used herein refers to straight-chained and branched alkynyl groups containing from 2 to 6 carbon atoms. Typical examples include ethynyl and propargyl groups.

Typical $C_{3-7}$ cycloalkyl groups include cyclopropyl, cyclobutyl, cyclopentyl and cyclohexyl.

Typical $C_{3-7}$ cycloalkyl($C_{1-6}$)alkyl groups include cyclopropylmethyl and cyclohexylmethyl.

Typical aryl groups include phenyl and naphthyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl and morpholinyl groups.

Suitable heteroaryl groups include pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The term "halogen" as used herein includes fluorine, chlorine, bromine and iodine, especially fluorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Certain compounds according to the present invention may be capable of existing as tautomeric forms. For example, a hydroxypyridine derivative in accordance with the invention may exist in admixture with its tautomeric pyridone isomer. It is to be understood that all possible tautomers and mixtures thereof in any proportion are encompassed within the scope of the present invention.

Where the compounds according to the invention have at least one asymmetric centre, they may accordingly exist as enantiomers. Where the compounds according to the invention possess two or more asymmetric centres, they may additionally exist as diastereoisomers. For example, the relative stereochemistry between the fluorine atom at the 3-position and the substituted amino moiety at the 4-position of the piperidine ring in the compounds of formula I as depicted above may be cis or trans. Moreover, the compounds of formula I above wherein Z represents a group of formula (Zb) or (Zc) have a chiral centre denoted by the asterisk *, which may accordingly be in the (R) or (S) configuration. It is to be understood that all such isomers and mixtures thereof in any proportion are encompassed within the scope of the present invention.

Where E and Q, which may be the same or different, represent straight or branched alkylene chains, these may be, for example, methylene, ethylene, 1-methylethylene, propylene, 2-methylpropylene or butylene. In addition, the alkylene chain Q may be substituted in any position by one or more substituents selected from fluoro and hydroxy giving rise, for example, to a 2-hydroxypropylene, 2-hydroxymethyl-propylene, 2-fluoropropylene or 2-fluoromethyl-propylene chain Q. Moreover, E may represent a chemical bond such that the moiety Z is attached directly to the central fused bicyclic heteroaromatic ring system containing the variables T, U and V.

Suitably, E represents a chemical bond or a methylene linkage.

Suitably, Q represents a propylene linkage.

The compound of formula I in accordance with the present invention is suitably an indole, benzofuran or benzthiophene derivative of formula IA, an indazole derivative of formula IB, or a pyrrolo[2,3-c]pyridine derivative of formula IC:

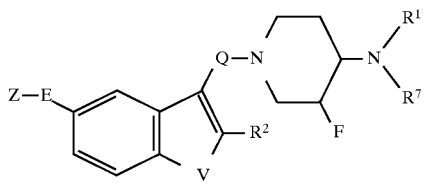
(IA)

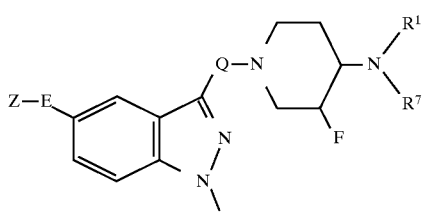
(IB)

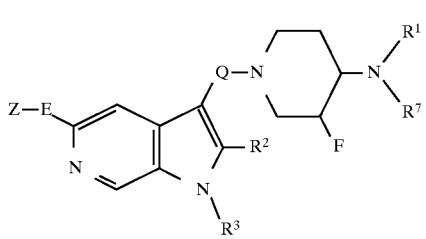
(IC)

wherein Z. E, Q, V, $R^1$, $R^2$, $R^3$ and $R^7$ are as defined above. Typically, the compounds according to the invention are indole or benzofuran derivatives of formula ID:

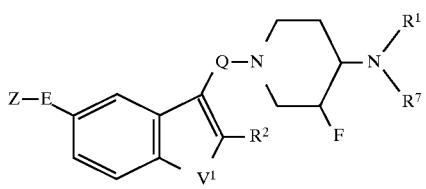
(ID)

wherein $V^1$ represents oxygen or N—$R^3$, preferably N—$R^3$, and Z, E, Q, $R^1$, $R^2$, $R^3$ and $R^7$ are as defined above, in particular wherein $R^2$ and $R^3$ are both hydrogen.

Suitable values for the substituent $R^1$ include benzyl, phenylethyl, phenylpropyl, furylmethyl, thienylmethyl, imidazolylmethyl and pyridinylmethyl, any of which groups may be optionally substituted by one or more substituents selected typically from halogen, cyano, trifluoromethyl, triazolyl, tetrazolyl, $C_{1-6}$ alkyl-tetrazolyl, hydroxy, keto, $C_{1-6}$ alkoxy, amino, di($C_{1-6}$)alkylamino, di($C_{1-6}$) alkylaminomethyl, $C_{2-6}$ alkylcarbonylamino, $C_{2-6}$ alkoxycarbonylamino, N-($C_{1-6}$)alkyl-N-($C_{2-6}$) alkoxycarbonylamino, $C_{1-6}$ alkylsulphonylamino, aminocarbonylamino, aminocarbonyl, $C_{1-6}$ alkylaminocarbonyl, di($C_{1-6}$)alkylaminocarbonyl, aminosulphonyl and $C_{1-6}$ alkylaminosulphonylmethyl.

Representative values of $R^1$ include benzyl, fluorobenzyl, difluorobenzyl, cyanobenzyl, trifluoromethyl-benzyl, tetrazolyl-benzyl, methyltetrazolyl-benzyl, methoxybenzyl, aminobenzyl, dimethylaminomethyl-benzyl, acetylaminobenzyl, aminocarbonyl-benzyl, methylaminocarbonyl-benzyl, dimethylaminocarbonyl-benzyl, aminosulphonyl-benzyl, 1-phenylethyl, 2-phenylethyl, fluoro-phenylethyl, difluoro-phenylethyl, cyano-phenylethyl, trifluoromethyl-phenylethyl, triazolyl-phenylethyl, 2-hydroxy-1-phenylethyl, phenylcarbonylmethyl, amino-phenylethyl, dimethylamino-phenylethyl, acetylamino-phenylethyl, methoxycarbonylamino-phenylethyl, (N-methyl-N-methoxycarbonyl)amino-phenylethyl, aminocarbonylamino-phenylethyl, 2-phenylpropyl, 3-phenylpropyl, furylmethyl, thienylmethyl, imidazolylmethyl, pyridylmethyl and amino-pyridylmethyl.

Particular values of $R^1$ include benzyl, trifluoromethyl-benzyl and 1-phenylethyl.

Suitably, $R^2$ and $R^3$ independently represent hydrogen or methyl, especially hydrogen.

Suitably, $R^4$ represents hydrogen or methyl.

Suitably, $R^5$ and $R^6$ are independently selected from hydrogen, methyl, ethyl, n-propyl, isopropyl, n-butyl, tert-butyl, trifluoromethyl, phenyl, methylphenyl (especially 4-methylphenyl), benzyl and phenethyl.

Suitably, $R^7$ represents hydrogen or methyl.

Suitably, the substituent Z represents hydrogen, fluoro, cyano, hydroxy, methoxy, ethoxy, benzyloxy, methylaminocarbonyloxy, cyanomethoxy, aminocarbonyl-methoxy, methylsulphonyl, aminosulphonyl, N-methylamino-sulphonyl, N N-dimethylamino-sulphonyl, amino, formylamino, acetylamino, trifluoromethyl-carbonylamino, benzyloxycarbonylamino, methyl-sulphonylamino, ethyl-sulphonylamino, methylphenyl-sulphonylamino, N-methyl-(N-methylsulphonyl)-amino, N-methyl-(N-ethylsulphonyl)-amino, N-methyl-(N-trifluoromethylsulphonyl)-amino, N-ethyl-(N-methylsulphonyl)-amino, N-benzyl-(N-methylsulphonyl)-amino, N-benzyl-(N-ethylsulphonyl)-amino, acetyl, methoxycarbonyl, ethoxycarbonyl, aminocarbonyl, methylaminocarbonyl, ethylaminocarbonyl, propylaminocarbonyl, butylaminocarbonyl, benzylaminocarbonyl or phenethyl-aminocarbonyl; or a group of formula (Za), (Zb), (Zc) or (Zd) as defined above; or an optionally substituted five-membered or six-membered heteroaromatic ring as specified above.

In a particular embodiment, Z represents —$SO_2NR^5R^6$ in which $R^5$ and $R^6$ are as defined above. In a subset of this embodiment, $R^5$ and $R^6$ independently represent hydrogen or $C_{1-6}$ alkyl, especially hydrogen or methyl. Particular values of Z in this context include aminosulphonyl, N-methylamino-sulphonyl and N,N-dimethylamino-sulphonyl, especially N-methylamino-sulphonyl.

In another embodiment, Z represents a group of formula (Zb) in which $R^4$ is hydrogen or methyl. In a subset of this embodiment, X and Y both represent oxygen. In a particular aspect of this subset, the chiral centre denoted by the asterisk * is in the (S) configuration.

When the group Z represents an optionally substituted five-membered heteroaromatic ring, this is suitably a 1,3-oxazole, 1,3-thiazole, imidazole, 1,2,4-oxadiazole, 1,3,4-oxadiazole, 1,2,4-thiadiazole, 1,3,4-thiadiazole, 1,2,3-triazole, 1,2,4-triazole or tetrazole ring. Preferably, the ring is a 1,3-oxazole, 1,3-thiazole, imidazole, 1,2,4-oxadiazole, 1,2,4-thiadiazole or 1,2,4-triazole ring, in particular an imidazol-1-yl, 1,2,4-triazol-1-yl or 1,2,4-triazol-4-yl moiety.

Suitably, the five-membered heteroaromatic ring as specified for Z is unsubstituted. Examples of optional substituents which may typically be attached to the moiety Z include methyl, ethyl, benzyl and amino.

When the group Z represents an optionally substituted six-membered heteroaromatic ring, this is suitably a pyridin-2-yl, pyridin-3-yl, pyridin-4-yl, pyrazin-2-yl, pyrazin-3-yl, pyrimidin-2-yl, pyrimidin-4-yl, pyrimidin-5-yl, pyridazin-3-yl or pyridazin-4-yl ring, especially pyridin-3-yl or pyrimidin-5-yl.

The six-membered heteroaromatic ring as specified for Z is unsubstituted or substituted by one or more substituents, typically by one or two substituents. Examples of optional substituents which may typically be attached to the moiety Z include methyl, methoxy, methoxycarbonyl, methoxymethyl, aminomethyl, dimethylaminomethyl, acetylaminomethyl, benzoylaminomethyl, tert-butoxycarbonylaminomethyl, methylsulphonylaminomethyl, phenylsulphonylaminomethyl, aminocarbonylmethyl, ethyl, aminoethyl, acetylaminoethyl, benzoylaminoethyl, methoxycarbonylaminoethyl, ethoxycarbonylaminoethyl, tert-butoxycarbonylaminoethyl, methylsulphonylaminoethyl, aminocarbonylaminoethyl, methylaminocarbonylaminoethyl, tert-butylaminocarbonylaminoethyl, phenylaminocarbonylaminoethyl, pyrrolidinylcarbonylaminoethyl, cyclopropyl, phenyl, naphthyl, benzyl, phenylethyl, phenylpropyl, pyridinylmethyl, amino, methylamino, dimethylamino, aminocarbonyl, methylaminocarbonyl, azetidinylcarbonyl and pyrrolidinylcarbonyl.

A particular sub-class of compounds according to the invention is represented by the compounds of formula IIA, and salts and prodrugs thereof:

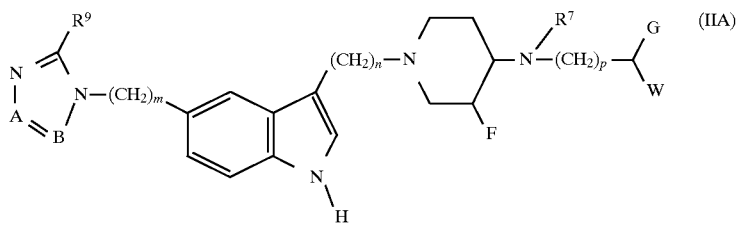

wherein m is zero, 1, 2 or 3, preferably zero or 1;

n is 2, 3 or 4, preferably 3;

p is zero, 1 or 2;

A represents nitrogen or CH;

B represents nitrogen or C—$R^{10}$;

$R^7$ is as defined with reference to formula I above;

$R^9$ and $R^{10}$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl;

G represents hydrogen, $C_{1-3}$ alkyl or hydroxy($C_{1-3}$)alkyl; and

W represents a group of formula (Wa), (Wb) or (Wc):

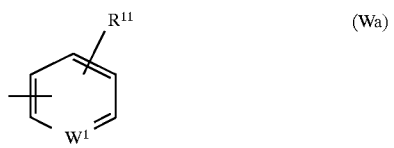

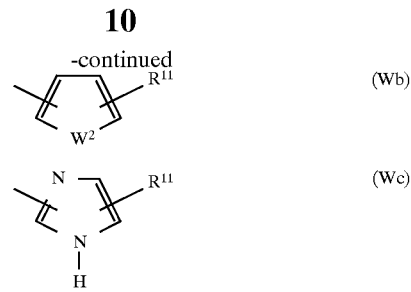

in which $W^1$ represents CH or nitrogen;

$W^2$ represents oxygen, sulphur, NH or N-methyl; and $R^{11}$ represents hydrogen, halogen, cyano, trifluoromethyl, triazolyl, tetrazolyl, $C_{1-6}$ alkyl-tetrazolyl, $C_{1-6}$ alkoxy, $C_{2-6}$ alkylcarbonyl, amino, $C_{1-6}$ alkylamino, di($C_{1-6}$)alkylamino, di($C_{1-6}$)alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl or $C_{1-6}$ alkylaminosulphonylmethyl.

Particular values of $R^9$ and $R^{10}$ include hydrogen, methyl, ethyl, benzyl and amino, especially hydrogen.

Particular values of $R^{11}$ include hydrogen, fluoro, cyano, trifluoromethyl, triazolyl, tetrazolyl, methyl-tetrazolyl, methoxy, amino, dimethylaminomethyl, acetylamino, aminocarbonylamino, methylaminocarbonyl and aminosulphonyl, especially hydrogen or trifluoromethyl.

Particular values of G include hydrogen and methyl.

Suitably, W represents a group of formula (Wa).

Suitably, $W^1$ represents CH.

Specific compounds within the scope of the present invention include:

cis-4-benzylamino-3-fluoro-1-{3-[5-(1,2,4-triazol-4-yl)-1H-indol-3-yl]propyl}piperidine;

cis-4-(N-benzyl-N-methylamino)-3-fluoro-1-{3-[5-(1,2,4-triazol-4-yl)-1H-indol-3-yl]propyl}piperidine;

trans-3-fluoro-4-[(1R)-1-phenylethylamino]-1-{3-[5-(1,2,4-triazol-4-yl)-1H-indol-3-yl]propyl}piperidine;

trans-3-fluoro-1-{3-[5-(1,2,4-triazol-4-yl)-1H-indol-3-yl]propyl}-4-[2-(trifluoromethyl)benzylamino]piperidine;

trans-3-fluoro-4-{N-methyl-N-[2-(trifluoromethyl)benzyl]amino}-1-{3-[5-(1,2,4-triazol-4-yl)-1H-indol-3-yl]propyl}piperidine;

cis-3-fluoro-1-{3-[5-(1,2,4-triazol-4-yl)-1H-indol-3-yl]propyl}-4-[2-(trifluoromethyl)benzylamino]piperidine;

cis-3-fluoro-4-{N-methyl-N-[2-(trifluoromethyl)benzyl]amino}-1-{3-[5-(1,2,4-triazol-4-yl)-1H-indol-3-yl]propyl}piperidine;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention wherein T represents CH, U represents C—$R^2$ and V represents N—$R^3$, corresponding to the indole derivatives of formula ID as defined above wherein $V^1$ represents N—$R^3$, may be prepared by a process which comprises reacting a compound of formula III:

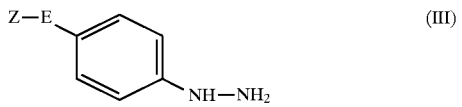

wherein Z and E are as defined above; with a compound of formula IV, or a carbonyl-protected form thereof:

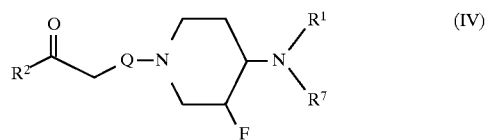

wherein $R^1$, $R^2$, $R^7$ and Q are as defined above; followed, where required, by N-alkylation by standard methods to introduce the moiety $R^3$.

The reaction between compounds III and IV, which is an example of the well-known Fischer indole synthesis, is suitably carried out by heating the reagents together under mildly acidic conditions, e.g. 4% sulphuric acid at reflux.

Suitable carbonyl-protected forms of the compounds of formula IV include the dimethyl acetal or ketal derivatives.

The Fischer reaction between compounds III and IV may be carried out in a single step, or may proceed via an initial non-cyclising step at a lower temperature to give an intermediate of formula V:

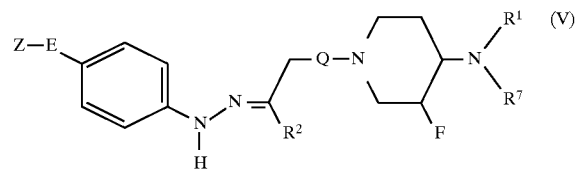

wherein Z, E, Q, $R^1$, $R^2$ and $R^7$ are as defined above; followed by cyclisation using a suitable reagent, e.g. a polyphosphate ester.

The intermediates of formula IV, or carbonyl-protected forms thereof, may be prepared by reacting a compound of formula VI, or a carbonyl-protected form thereof, with a compound of formula VII:

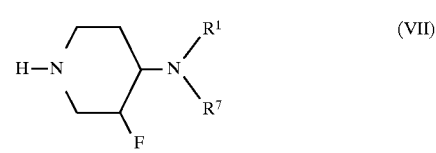

wherein Q, $R^1$, $R^2$ and $R^7$ are as defined above, and $L^1$ represents a suitable leaving group.

The leaving group $L^1$ is suitably a halogen atom, e.g. chlorine or bromine.

Where $L^1$ represents a halogen atom, the reaction between compounds VI and VII is conveniently effected by stirring the reactants under basic conditions in a suitable solvent, for example sodium carbonate in 1,2-dimethoxyethane, typically in the presence of sodium iodide.

Where the alkylene chain Q is substituted by a hydroxy group, this group may condense with the carbonyl moiety in compound IV, whereby the carbonyl moiety is protected in the form of a cyclic hemiacetal.

In an alternative procedure, the compounds according to the invention may be prepared by a process which comprises reacting a compound of formula VII as defined above with a compound of formula VIII:

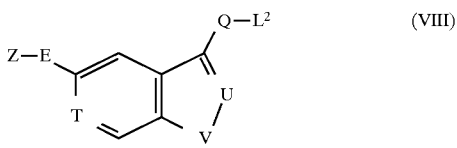

wherein Z, E, Q, T, U and V are as defined above, and $L^2$ represents a suitable leaving group.

The leaving group $L^2$ is suitably an alkylsulphonyloxy or arylsulphonyloxy group, e.g. methanesulphonyloxy (mesyloxy) or p-toluenesulphonyloxy (tosyloxy).

Where $L^2$ represents an alkylsulphonyloxy or arylsulphonyloxy group, the reaction between compounds VII and VIII is conveniently carried out in a suitable solvent such as 1,2-dimethoxyethane or isopropyl alcohol, optionally in the presence of a cosolvent such as acetonitrile, typically in the presence of a base such as sodium carbonate or potassium carbonate, and optionally with the addition of sodium iodide.

In one representative approach, the compounds of formula VIII wherein T and U both represent CH, V represents NH and $L^2$ represents a mesyloxy or tosyloxy group may be prepared by the sequence of steps illustrated in the following reaction scheme (cf. Larock and Yum, *J. Am. Chem. Soc.*, 1991, 113, 6689):

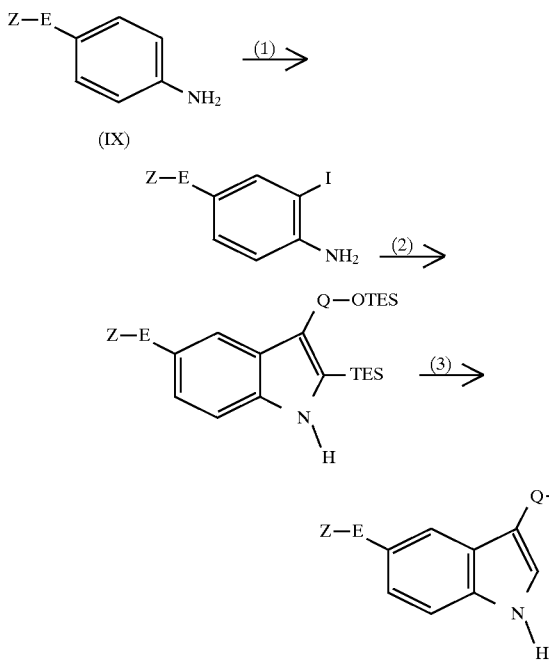

wherein Z, E and Q are as defined above, $L^3$ represents mesyloxy or tosyloxy, and TES is an abbreviation for triethylsilyl.

In Step 1 of the reaction scheme, the aniline derivative IX is treated with iodine monochloride, typically in methanol or acetonitrile, in order to introduce an iodine atom ortho to the amine moiety. Step 2 involves a palladium-mediated coupling reaction with the protected acetylene derivative TES—C≡C—Q—OTES, typically using palladium acetate and triphenylphosphine in the presence of lithium chloride and sodium carbonate, suitably in N,N-dimethylformamide at an elevated temperature. This is followed in Step 3 by removal of the TES moiety, typically by treatment with hydrochloric acid; followed in turn by mesylation or tosylation, suitably by using mesyl chloride or tosyl chloride respectively in the presence of a base such as triethylamine or pyridine, typically in dichloromethane/acetonitrile.

In another representative approach, the compounds of formula VIII wherein T and U both represent CH, V represents NH, Q represents a propylene chain and $L^2$ represents a mesyloxy or tosyloxy group may be prepared by reacting 3,4-dihydro-2H-pyran with a compound of formula III as defined above or a salt thereof, under a variant of the Fischer reaction conditions as described above for the reaction between compounds III and IV; followed by mesylation or tosylation of the 3-hydroxypropylindole derivative thereby obtained, typically by treatment with mesyl chloride or tosyl chloride under standard conditions.

The Fischer reaction with 3,4-dihydro-2H-pyran is suitably brought about by stirring the pyran derivative with an acid addition salt of the hydrazine derivative III, typically the hydrochloride salt, in an inert solvent such as aqueous ethanol. The resulting hydrazide derivative can then be cyclised by treatment with a Lewis acid such as zinc chloride, in a solvent such as 1,2-dimethoxyethane, suitably at the reflux temperature of the solvent.

In another procedure, the compounds according to the invention wherein E represents a chemical bond may be prepared by reacting a compound of formula X with a compound of formula XI:

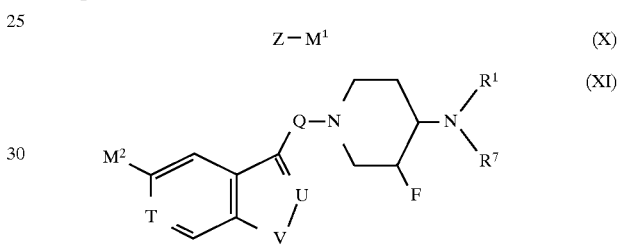

wherein Z, Q, T, U, V, $R^1$ and $R^7$ are as defined above; one of $M^1$ and $M^2$ represents a suitable leaving group, and the other represents a boronic acid moiety —$B(OH)_2$ or a $C_{1-4}$ alkyl ester or anhydride thereof; in the presence of a transition metal catalyst.

The leaving group $M^1$ or $M^2$ is suitably a halogen atom, e.g. bromine.

The transition metal catalyst of use in the reaction between compounds X and XI is suitably tetrakis(triphenylphosphine)palladium (0). The reaction is conveniently carried out in an inert solvent such as aqueous 1,2-dimethoxyethane, advantageously in the presence of a base such as sodium acetate or sodium carbonate, typically at an elevated temperature.

In a further procedure, the compounds according to the invention wherein T represents CH, U represents nitrogen and V represents N—$R^3$, corresponding to the indazole derivatives of formula IB as defined above, may be prepared by a process which comprises cyclising a compound of formula XII:

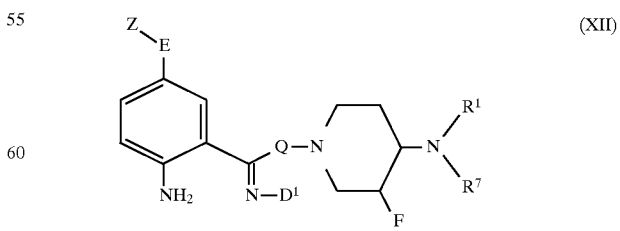

wherein Z, E, Q, $R^1$ and $R^7$ are as defined above, and $D^1$ represents a readily displaceable group; followed, where required, by N-alkylation by standard methods to introduce the moiety $R^3$.

The cyclisation of compound XII is conveniently achieved in a suitable organic solvent at an elevated temperature, for example in a mixture of m-xylene and 2,6-lutidine at a temperature in the region of 140° C.

The readily displaceable group $D^1$ in the compounds of formula XII suitably represents a $C_{1-4}$ alkanoyloxy group, preferably acetoxy. Where $D^1$ represents acetoxy, the desired compound of formula XII may be conveniently prepared by treating a carbonyl compound of formula XIII:

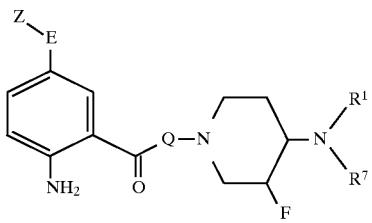
(XIII)

wherein Z, E, Q, $R^1$ and $R^7$ are as defined above; or a protected derivative thereof, preferably the N-formyl protected derivative; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivatives of the intermediates of formula XIII may conveniently be prepared by ozonolysis of the corresponding indole derivative of formula XIV:

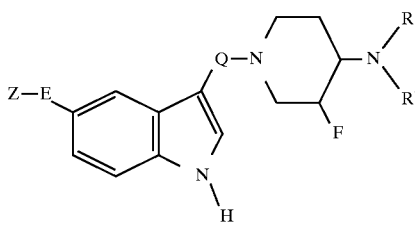
(XIV)

wherein Z, E, Q, $R^1$ and $R^7$ are as defined above; followed by a reductive work-up, advantageously using dimethylsulphide.

The indole derivatives of formula XIV may be prepared by methods analogous to those described in the accompanying Examples, or by procedures well known from the art.

In a still further procedure, the compounds according to the invention wherein T represents CH, U represents C—$R^2$ and V represents oxygen or sulphur, corresponding to the benzofuran or benzthiophene derivatives of formula IA wherein V is oxygen or sulphur respectively, may be prepared by a process which comprises cyclising a compound of formula XV:

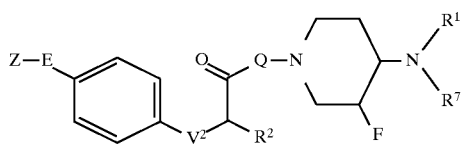
(XV)

wherein Z, E, Q, $R^1$, $R^2$ and $R^7$ are as defined above, and $V^2$ represents oxygen or sulphur.

The cyclisation of compound XV is conveniently effected by using polyphosphoric acid or a polyphosphate ester, advantageously at an elevated temperature.

The compounds of formula XV may be prepared by reacting a compound of formula XVI with a compound of formula XVII:

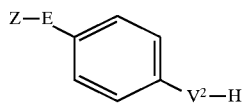
(XVI)

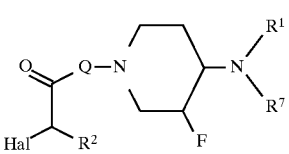
(XVII)

wherein Z, E, Q, $R^1$, $R^2$, $R^7$ and $V^2$ are as defined above, and Hal represents a halogen atom.

The reaction is conveniently effected in the presence of a base such as sodium hydroxide.

The hydroxy and mercapto derivatives of formula XVI may be prepared by a variety of methods which will be readily apparent to those skilled in the art. One such method is described in EP-A-0497512.

In a yet further procedure, the compounds according to the invention may be prepared by a process which comprises reducing a compound of formula XVIII:

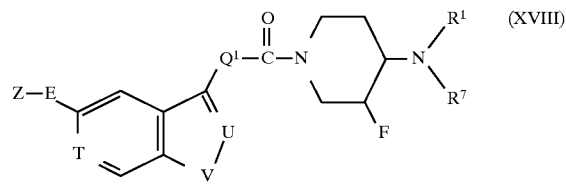
(XVIII)

wherein Z, E, T, U, V, $R^1$ and $R^7$ are as defined above, and —$Q^1$—$CH_2$— corresponds to the moiety Q as defined above.

The reaction is suitably carried out by treating the compound of formula XVIII with a reducing agent such as lithium aluminium hydride in an appropriate solvent, e.g. diethyl ether or tetrahydrofuran, or mixtures thereof.

The compounds of formula XVIII above may suitably be prepared by reacting a compound of formula VII as defined above with a compound of formula XIX:

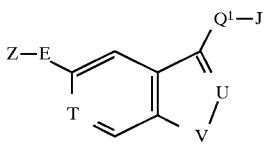
(XIX)

wherein Z, E, T, U, V and $Q^1$ are as defined above, and J represents a reactive carboxylate moiety.

Suitable values for the reactive carboxylate moiety J include esters, for example $C_{1-4}$ alkyl esters; acid anhydrides, for example mixed anhydrides with $C_{1-4}$ alkanoic acids; acid halides, for example acid chlorides; and acylimidazoles.

By way of example, the intermediates of formula XIX above wherein J is an acid chloride moiety may be prepared by treating the corresponding carboxylic acid derivative with thionyl chloride in toluene. Similarly, the intermediates of formula XIX wherein J is an acylimidazole moiety may be prepared by treating the corresponding carboxylic acid derivative with 1, 1'-carbonyldiimidazole. Alternatively, the reactive carboxylate moiety J may be obtained by treating the corresponding compound wherein J is carboxy with 1-(3-dimethylaminopropyl)-3-ethylcarbodiimide hydrochloride and 1-hydroxybenzotriazole hydrate, optionally in the presence of triethylamine; the resulting activated carboxylate intermediate may then suitably be reacted in situ with the required compound of formula VII.

In one additional procedure, the compounds according to the invention may be prepared by a process which comprises reacting a compound of formula VII as defined above with a compound of formula XX:

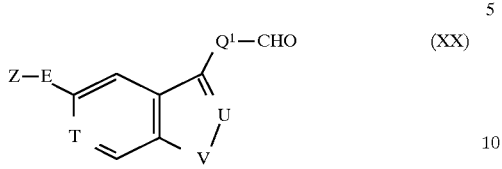

wherein Z, E, T, U, V and $Q^1$ are as defined above; in the presence of a reducing agent.

Moreover, the compounds of formula XI above may be prepared by reacting a compound of formula VII as defined above with a compound of formula XXI:

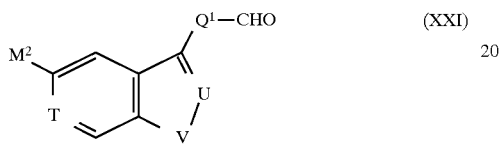

wherein T, U, V, $M^2$ and $Q^1$ are as defined above; in the presence of a reducing agent.

A suitable reducing agent for use in conjunction with the above 15 reaction between compound VII and compound XX or XXI is sodium triacetoxyborohydride, in which case the reaction is conveniently effected in the presence of acetic acid and a solvent such as dichloromethane.

The compounds of formula XX and XXI may be prepared by reduction of the appropriate compound of formula XXII:

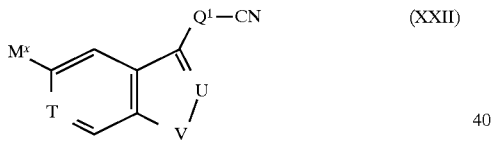

wherein T, U, V and $Q^1$ are as defined above; and $M^x$ corresponds to the moiety Z—E— as defined above, or $M^x$ corresponds to the group of formula $M^2$ as defined above.

A suitable reducing agent for effecting the transformation of the cyano moiety in compound XXII to the carboxaldehyde (CHO) moiety in compounds XX and XXI is diisobutylaluminium hydride (DIBAL-H), and the reaction is conveniently carried out in a solvent such as dichloromethane.

A representive approach to the nitrile intermediates of formula XXII in which T and U both represent CH, V is oxygen and $Q^1$ is an ethylene linkage can be illustrated as follows:

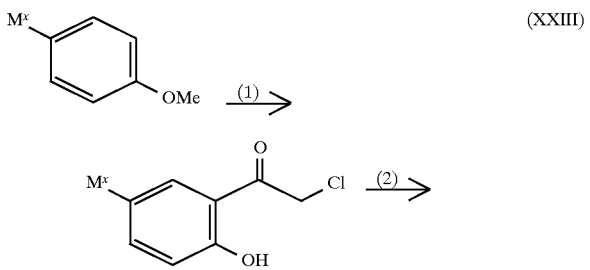

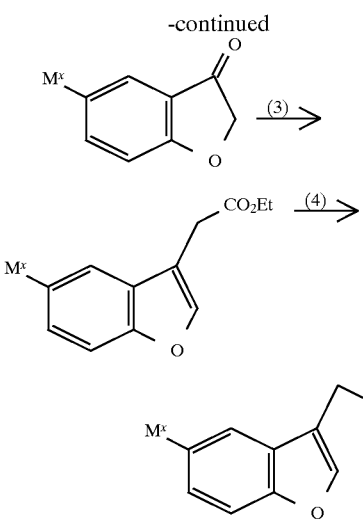

in which $M^x$ is as defined above.

In Step 1, the anisole derivative XXIII is treated with chloroacetyl chloride in the presence of aluminium chloride, whereby the methoxy substituent is demethylated, with concomitant introduction of the chloroacetyl moiety ortho to the resulting phenolic OH. This compound is then cyclised in Step 2, by treatment with methanolic sodium acetate at an elevated temperature. Step 3 comprises treatment of the resulting furanone derivative with triethylphosphonoacetate in the presence of a strong base such as potassium hexamethyldisilazide, followed in Step 4 by DIBAL-H reduction of the ethyl ester moiety in the resulting compound. The hydroxyethyl benzofuran derivative thereby obtained is mesylated, and the mesyl group thereof subsequently displaced by cyanide ion, to afford the desired cyanoethyl benzofuran analogue.

The intermediates of formula XI above may suitably be prepared by reacting a compound of formula VII as defined above with a compound of formula XXIV:

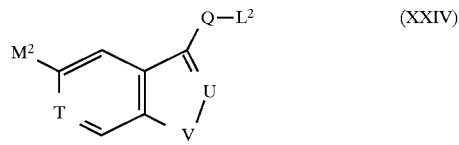

wherein Q, T, U, V, $L^2$ and $M^2$ are as defined above; under conditions analogous to those described above for the reaction between compounds VII and VIII.

Typical intermediates of formula XXIV, wherein T and U are both CH, V is oxygen, Q is an ethylene linkage and $L^2$ is mesyl or tosyl, can be prepared from compound XXIII, in which $M^x$ corresponds to the group $M^2$, by following Steps 1 to 3 of the reaction scheme illustrated immediately above to obtain the ethyl ester intermediate, which can then be reduced with DIBAL-H and mesylated or tosylated under standard conditions.

The hydrazine derivatives of formula III above may be prepared by methods analogous to those described in EP-A-0438230, EP-A-0497512, EP-A-0548813 and WO-A-91/18897, as also may the aniline derivatives of formula IX.

Where they are not commercially available, the starting materials of formula VI, VII, X, XVII, XIX and XXIII may be prepared by methods analogous to those described in the accompanying Examples, or by standard procedures well known from the art.

It will be understood that any compound of formula I initially obtained from any of the above processes may, where appropriate, subsequently be elaborated into a further compound of formula I by techniques known from the art. For example, a compound of formula I wherein $R^7$ is hydrogen initially obtained may be converted into a corresponding compound wherein $R^7$ is $C_{1-3}$ alkyl using standard N-alkylation techniques, for example reductive alkylation using the appropriate aldehyde or ketone in the presence of a reducing agent such as sodium cyanoborohydride, typically in acetic acid and methanol at room temperature. Furthermore, a compound of formula I initially obtained wherein the $R^1$ moiety is substituted by nitro or cyano may be converted by catalytic hydrogenation to the corresponding amino- or aminomethyl-substituted compound respectively. Additionally, a compound of formula I wherein the $R^1$ moiety is substituted by hydroxy, possibly obtained by lithium aluminium hydride reduction of a precursor alkoxycarbonyl derivative, may be mesylated under standard conditions, and the mesyl group subsequently displaced by an amino moiety by treatment with the desired amine in a sealed tube at an elevated temperature. The amine derivative resulting from any of these procedures may then, for example, be N-acylated using the appropriate acyl halide, e.g. acetyl chloride; or aminocarbonylated, using potassium isocyanate, to the corresponding urea derivative; or converted to a 1,2,4-triazol-4-yl derivative using N,N-dimethylformamide azine; or reductively alkylated by treatment with the appropriate aldehyde or ketone in the presence of sodium cyanoborohydride. If desired, the amine derivative may also be carbamoylated by treatment with the requisite alkyl chloroformate. A compound of formula I initially obtained wherein the $R^1$ moiety is substituted by cyano may be converted, by treatment with sodium azide, to the corresponding tetrazole derivative, which in turn may be alkylated on the tetrazole ring by treatment with an alkyl halide under standard conditions. By way of additional illustration, a compound of formula I initially obtained wherein the $R^1$ moiety is substituted by an alkoxycarbonyl moiety may be saponified, by treatment with an alkali metal hydroxide, to the corresponding carboxy-substituted compound, which in turn may be converted to an amide derivative by treatment with the appropriate amine, advantageously in the presence of 1-(3-dimethylaminopropyl)-3-ethylcarbodiimide hydrochloride and 1-hydroxybenzotriazole. Moreover, a compound of formula I wherein $R^3$ is hydrogen initially obtained may be converted into a compound of formula I wherein $R^3$ represents $C_{1-6}$ alkyl by standard alkylation techniques, for example by treatment with an alkyl iodide, e.g. methyl iodide, typically under basic conditions, e.g. sodium hydride in N,N-dimethylformamide.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups Organic Chemistry*, ed. J. F. W. McOmie, Plenum Press, 1973; and T. W. Greene & P. G. M. Wuts, *Protective Groups it Organic Synthesis*, John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the 5-HT$_{1D_\alpha}$ receptor subtype, inhibit forskolin-stimulated adenylyl cyclase activity, and stimulate [$^{35}$S]-GTPγS binding to membranes from clonal cell lines expressing human cloned receptors.

5-HT$_{1D_\beta}$/5-HT$_{1D_\beta}$ Radioligand Binding

Chinese hamster ovary (CHO) clonal cell lines expressing the human 5-HT$_{1D_\alpha}$ and 5-HT$_{1D_\beta}$ receptors were harvested in PBS and homogenised in ice cold 50 mM Tris-HCl (pH 7.7 at room temperature) with a Kinematica polytron and centrifuged at 48,000 g at 4° C. for 11 min. The pellet was then resuspended in 50 mM Tris-HCl followed by a 10 min incubation at 37° C. Finally the tissue was recentrifuged at 48,000 g, 4° C. for 11 min and the pellet resuspended, in assay buffer (composition in mM: Tris-HCl 50, pargyline 0.01, CaCl$_2$ 4; ascorbate 0.1%; pH 7.7 at room temperature) to give the required volume immediately prior to use (0.2 mg protein/ml). Incubations were carried out for 30 min at 37° C. in the presence of 0.02–150 nM [$^3$H]-5-HT for saturation studies or 2–5 nM [$^3$H]-5-HT for displacement studies. The final assay volume was 1 ml. 5-HT (10 $\mu$M) was used to define non-specific binding. The reaction was initiated by the addition of membrane and was terminated by rapid filtration through Whatman GF/B filters (presoaked in 0.3% PEI/0.5% Triton X) followed by 2×4 ml washings with 50 mM Tris-HCl. The radioactive filters were then counted on a LKB beta or a Wallac beta plate counter. Binding parameters were determined by non-linear, least squares regression analysis using an iterative curve fitting routine, from which IC$_{50}$ (the molar concentration of compound necessary to inhibit binding by 50%) values could be calculated for each test compound. The IC$_{50}$ values for binding to the 5-HT$_{1D_\alpha}$ receptor subtype obtained for the compounds of the accompanying Examples were below 50 nM in each case. Furthermore, the compounds of the accompanying Examples were all found to possess a selective affinity for the 5-HT$_{1D_\alpha}$ receptor subtype of at least 10-fold relative to the 5-HT$_{1D_\beta}$ subtype.

5-HT$_{1D_\alpha}$/5-HT$_{1D_\beta}$ Adenylyl Cyclase Assay

Studies were performed essentially as described in *J. Pharmacol. Exp. Ther.,* 1986, 238, 248. CHO clonal cell lines expressing the human cloned 5-HT$_{1D_\alpha}$ and 5-HT$_{1D_\beta}$ receptors were harvested in PBS and homogenised, using a motor driven teflon/glass homogeniser, in ice cold Tris HCl-EGTA buffer (composition in mM: Tris HCl 10, EGTA 1, pH 8.0 at room temperature) and incubated on ice for 30–60 min. The tissue was then centrifuged at 20,000 g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of α-[$^{33}$P]-ATP to [$^{33}$P]-cyclic AMP. A 10 μl aliquot of the membrane suspension was incubated, for 10–15 min, in a final volume of 50 μ, at 30° C., with or without forskolin (10 μM), in the presence or absence of test compound. The incubation buffer consisted of 50 mM Tris HCl (pH 7.6 at room temperature), 100 mM NaCl, 30 μM GTP, 50 μM cyclic AMP, 1 mM dithiothreitol, 1 mM ATP, 5 mM MgCl$_2$, 1 mM EGTA, 1 mM 3-isobutyl-1-methylxanthine, 3.5 mM creatinine phosphate, 0.2 mg/ml creatine phosphokinase, 0.5–1 μCi α-[$^{33}$P]-ATP and 1 nCi [$^3$H]-cyclic AMP. The incubation was initiated by the addition of membrane, following a 5 min preincubation at 30° C., and was terminated by the addition of 100 μl SDS (composition in mM: sodium lauryl sulphate 2%, ATP 45, cyclic AMP 1.3, pH 7.5 at room temperature). The ATP and cyclic AMP were separated on a double column chromatography system (*Anal. Biochem.*, 1974, 58, 541). Functional parameters were determined using a least squares curve fitting programme ALLFIT (*Am. J. Physiol.*, 1978, 235, E97) from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the 5-HT$_{1D_α}$ receptor obtained for the compounds of the accompanying Examples were below 500 nM in each case. Moreover, the compounds of the accompanying Examples which were tested were all found to possess at least a 10-fold selectivity for the 5-HT$_{1D_α}$ receptor subtype relative to the 5-HT$_{1D_β}$ subtype.

5-HT$_{1D_α}$/5-HT$_{1D_β}$ GTPγS Binding

Studies were performed essentially as described in *Br. J. Pharmacol.*, 1993, 109, 1120. CHO clonal cell lines expressing the human cloned 5-HT$_{1D_β}$ and 5-HT$_{1D_α}$ receptors were harvested in PBS and homogenised using a Kinematica polytron in ice cold 20 mM HEPES containing 10 mM EDTA, pH 7.4 at room temperature. The membranes were then centrifuged at 40,000 g, 4° C. for 15 min. The pellet was then resuspended in ice cold 20 mM HEPES containing 0.1 mM EDTA, pH 7.4 at room temperature and recentrifuged at 40,000 g, 4° C. for 15–25 minutes. The membranes were then resuspended in assay buffer (composition in mM: HEPES 20, NaCl 100, MgCl$_2$ 10, pargyline 0.01; ascorbate 0.1%; pH 7.4 at room temperature) at a concentration of 40 μg protein/ml for the 5-HT$_{1D_α}$ receptor transfected cells and 40–50 μg protein/ml for the 5-HT$_{1D_β}$ receptor transfected cells. The membrane suspension was then incubated, in a volume of 1 ml, with GDP (100 μM for 5-HT$_{1D_α}$ receptor transfected cells, 30 μM for the 5-HT$_{1D_β}$ receptor transfected cells) and test compound at 30° C. for 20 min and then transferred to ice for a further 1.5 min. [$^{35}$S]-GTPγS was then added at a final concentration of 100 pM and the samples incubated for 30 min at 30° C. The reaction was initiated by the addition of membrane and was terminated by rapid filtration through Whatman GF/B filters and washed with 5 ml water. The radioactive filters were then counted on a LKB beta counter. Functional parameters were determined by a non-linear, least squares regression analysis using an iterative curve fitting routine, from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the 5-HT$_{1D_α}$ receptor obtained for the compounds of the accompanying Examples were below 500 nM in each case. Moreover, the compounds of the accompanying Examples which were tested were all found to possess at least a 10-fold selectivity for the 5-HT$_{1D_α}$ receptor subtype relative to the 5-HT$_{1D_β}$ subtype.

EXAMPLE 1 cis-4-Benzylamino-3-fluoro-1-{3-[5-(1,2,4-triazol-4-yl)-1H-indol-3-yl]propyl}piperidine, oxalate salt Step 1 1-tert-Butoxycarbonyl-1,2,3,6-tetrahydro-4-(trimethylsilyloxy)pyridine To a stirred solution of 1-tert-butoxycarbonyl-4-piperidone (10.13 g, 50.8 mmol) in anhydrous DMF (20 mL) under argon was added chlorotrimethylsilane (7.74 mL, 61.0 mmol), then anhydrous triethylamine (17.0 mL, 122 mmol) and the mixture was stirred at 80° C. for 16 h under argon. The mixture was partitioned between hexane (60 mL) and cold saturated NaHCO$_3$ solution (50 mL). The organic layer was washed with more cold saturated NaHCO$_3$ solution (2×30 mL), dried (Na$_2$SO$_4$) and evaporated in vacuo. The residue was purified by flash chromatography (silica gel, 10% EtOAc/petroleum ether) to give 11.84 g (86%) of the title compound as a colourless oil. $δ_H$ (250 MHz, CDCl$_3$) 0.20 (9H, s), 1.47 (9H, s), 2.11 (2H, m), 3.52 (2H, t, J=5.8 Hz), 3.87 (2H, m), 4.80 (1H, m).

Step 2 1-tert-Butoxycarbonyl-3-fluoro-4-piperidone

To a stirred solution of 1-tert-butoxycarbonyl-1,2,3,6-tetrahydro-4-(trimethylsilyloxy)pyridine (400 g, 14.7 mmol) in anhydrous acetonitrile (160 mL) under nitrogen was added Selectfluor™ reagent (5.74 g, 16.2 mmol) and the mixture was stirred for 75 min. The mixture was poured into ethyl acetate (600 mL), washed with diluted brine (300 mL), then saturated NaCl solution (100 mL), dried (MgSO$_4$) and evaporated in vacuo. The residue was purified by flash chromatography (alumina, 0–5% MeOH/EtOAc) to afford 2.91 g (91%) of the title compound as a colourless oil. $δ_H$ (250 MHz, CDCl$_3$) 1.50 (9H, s), 2.52–2.64 (2H, m), 3.22–3.38 (2H, m), 4.18 (1H, m), 4.45 (1H, m), 4.83 (1H, m).

Step 3 cis and trans-4-Benzylamino-1-tert-butoxycarbonyl-3-fluoropiperidine

A mixture of 1-tert-butoxycarbonyl-3-fluoro-4-piperidone (0.1105 g, 0.509 mmol), benzylamine (61 μL, 0.559 mmol) and sodium triacetoxyborohydride (0.1628 g, 0.768 mmol) in anhydrous 1,2-dichloroethane (2 mL) was stirred at room temperature under nitrogen for 135 min. The reaction mixture was quenched with saturated K$_2$CO$_3$ solution (20 mL) and extracted with ethyl acetate (2×20 ml,). The combined organic extracts were dried (Na$_2$SO$_4$) and evaporated in vacuo. The residue was purified by flash chromatography (silica gel, 50–100% EtOAc/hexane) to give 12.7 mg (8%) of the trans isomer and 99.5 mg (63%) of the cis isomer of the title compound as colourless oils.

trans isomer: $δ_H$ (360 MHz, d$_6$-DMSO) 1.34 (1H, m), 1.39 (9H, s), 1.81 (1H, m), 2.74 (1H, m), 3.14 (1H, m), 3.30 (1H, m), 3.48 (1H, m), 3.69 (1H, m), 3.77 (2H, m), 4.39 (1H, m), 7.22 (1H, m), 7.28–7.35 (4H, m); m/e (ES+) 309 (M+H)$^+$, 253 (M−CMe$_3$+2H)$^+$.

cis isomer: $δ_H$ (360 MHz, d$_6$-DMSO) 1.38 (9H, s), 1.44 (1H, m), 1.68 (1H, m), 2.64 (1H, m), 2.74 (1H, m), 2.96 (1H, m), 3.78 (1H, m), 4.14 (1H, m), 4.78 (1H, m), 7.21 (1H, m), 7.28–7.36 (4H, m); m/e (ES+) 309 (M+H)$^+$, 253 (M−CMe$_3$+2H)$^+$.

Step 4 cis-4-Benzylamino-3-fluoropiperidine

To a solution of cis-4-benzylamino-1-tert-butoxycarbonyl-3-fluoropiperidine (0.9087 g, 2.95 mmol) in anhydrous dichloromethane (5 mL) under argon was added trifluoroacetic acid (2.5 mL) and the solution was stirred at room temperature under argon for 140 min. Anhydrous methanol (1 mL) was added and the solvents were removed in vacuo. More methanol (2 mL) was added and removed in vacuo. The residue was partitioned between CH$_2$Cl$_2$ (30 mL) and dilute NaOH solution (20 mL). The aqueous layer was further extracted with CH$_2$Cl (30 ml×2) and the combined organic extracts were washed with brine (50 mL), dried (Na$_2$SO$_4$) and evaporated in vacuo to give 0.5756 g (94%) of the title compound as a colourless oil. $\delta_H$ (250 MHz, CDCl$_3$) 1.54 (1H, qd, J=12.0 and 4.1 Hz), 1.83 (1H, m), 2.54–2.76 (3H, m), 3.11 (1H, m), 3.88 (2H, m), 4.73 (1H, m), 7.23–7.37 (5H, m).

Step 5 cis-4-Benzylamino-3-fluoro-1-{3-[5-(1,2,4-triazol-4-yl)-1H-indol-3-yl]propyl}piperidine, oxalate salt To a stirred suspension of 3-[5-(1,2,4-triazol-4-yl)-1H-indol-3-yl]propan-1-ol (0.3018 g, 1.25 mmol) (WO 95/32196) in anhydrous THF (40 ml) under argon was added anhydrous triethylamine (0.347 mL, 2.49 mmol), then methanesulphonyl chloride (0.197 mL, 2.49 mmol) and the mixture was stirred at room temperature for 90 min. The mixture was then diluted with EtOAc (140 mL), washed with saturated NaCl solution (40 mL), dried (MgSO$_4$) and evaporated in vacuo.

The residue was dissolved in anhydrous 2-propanol (40 mL) and potassium chloride (0.3459 g, 2.50 mmol) was added, followed by a solution of cis-4-benzylamino-3-fluoropiperidine (0.3890 g, 1.87 mmol) in anhydrous 2-propanol (10 mL). The mixture was stirred at reflux under argon for 18 h. The solvent was evaporated in vacuo and the residue was partitioned between CH$_2$Cl$_2$ (50 mL) and water (20 mL). The aqueous layer was reextracted with more CH$_2$Cl$_2$ (2×50 mL). The combined organic extracts were washed with saturated NaCl solution, dried (Na$_2$SO$_4$) and evaporated in vacuo. The residue was purified by flash chromatography (silica gel, CH$_2$Cl$_2$—MeOH—NH$_3$ (aq); 92:8:0.8) to give 0.2088 g (39%) of the title compound, free base as a colourless oil. The oxalate salt was prepared in MeOH—Et$_2$O; mp 141°–149° C. Found: C, 54.17; H, 5.45; N, 12.72. C$_{25}$H$_{29}$FN$_6$. 2C$_2$H$_2$O$_4$. 1.7H$_2$O requires: C, 54.15; H, 5.70; N, 13.07%. $\delta_H$ (360 MHz, d$_6$-DMSO) 1.86–2.00 (4H, m), 2.34 (1H, m), 2.60–2.75 (5H, m), 3.10–3.26 (2H, m), 3.40 (1H, m), 4.12 (2H, m), 5.13 (1H, d, J=48.3 Hz), 7.30–7.33 (2H, m), 7.38–7.43 (3H, m), 7.48–7.51 (3H, m), 7.78 (1H, d, J=2.0 Hz), 11.14 (1H, s). m/e (ES+) 433 (M+H)$^+$.

EXAMPLE 2 cis-4-(N-Benzyl-N-methylamino)-3-fluoro-1-{3-[5-(1,2,4-triazol-4-yl)-1H-indol-3-yl]propyl}piperidine, oxalate salt To a stirred solution of cis-4-benzylamino-3-fluoro-1-{3-[5-(1,2,4-triazol-4-yl)-1H-indol-3-yl]propyl}piperidine (0.1216 g, 0.281 mmol) in anhydrous methanol (4 mL), under argon, was added glacial acetic acid (64.4 µL, 1.12 mmol), 37% wt solution of formaldehyde (25.3 µL, 0.338 mmol) and sodium cyanoborohydride (20.8 mg, 0.331 mmol) and the mixture was stirred at room temperature for 3 h. The mixture was quenched with saturated K$_2$CO$_3$ solution (10 mL) and extracted with ethyl acetate (2×25 mL). The combined organic extracts were dried (Na$_2$SO$_4$) and evaporated in vacuo. The residue was purified by flash chromatography (silica gel, CH$_2$Cl$_2$—MeOH—NH$_3$ (aq); 94:6:0.6 to 93:7:0.7) to give 0.1161 g (93%) of the title compound, free base as a colourless oil. The oxalate salt was prepared in MeOH—Et$_2$O; mp 111°–115° C. Found: C, 57.11; H, 5.84; N, 13.34. C$_{26}$H$_{31}$FN$_6$. 2C$_2$H$_2$O$_4$ requires: C, 57.50; H, 5.63; N, 13.41%. $\delta_H$ (360 MHz, d$_6$-DMSO) 1.87–2.12 (4H, m), 2.24 (3H, s), 2.74–3.04 (7H, m), 3.38 (1H, m), 3.59 (1H, m), 3.71 (2H, m), 5.24 (1H, d, J=50.2 Hz), 7.25–7.35 (7H, m), 7.50 (1H, d, J=8.5 Hz), 7.80 (1H, d, J=1.9 Hz), 11.17 (1H, s). m/e (ES+) 447 (M+H)$^+$.

EXAMPLE 3 tran-3-Fluoro-4-[(1R)-1-phenylethylamino]-1-{3-[5-(1,2,4-triazol-4yl)-1H-indol-3-yl]propyl}piperidine, oxalate salt Step 1 cis and trans-1-tert-Butoxycarbonyl-3-fluoro-4-[(1R)-1-phenylethylamino]piperidine Using a similar procedure to that described in Example 1, step 3, 1-tert-butoxycarbonyl-3-fluoro-4-piperidone (0.7272 g, 3.35 mmol) was reacted with (R)-α-methylbenzylamine (0.470 mL, 3.69 mmol) and sodium triacetoxyborohydride (1.066 g, 5.03 mmol) in 1,2-dichloroethane (13 mL). Purification by flash chromatography (silica gel, 40% EtOAc/hexane, then alumina, 80–100% CH$_2$Cl$_2$/hexane) gave 0.1204 g (11%) of the tracs isomer and 0.6082 g (56%) of the cis isomer of the title compound as colourless oils.

trans isomer: $\delta_H$ (250 MHz, CDCl$_3$) 1.18 (1H, m), 1.36 (3H, d, J=6.6 Hz), 1.43 (9H, s), 1.70 (1H, m), 2.63–2.80 (2H, m), 2.88 (1H, m), 3.73 (1H, m), 3.98 (1H, q, J=6.7 Hz), 4.19–4.39 (2H, m), 7.22–7.27 (1H, m), 7.31–7.33 (4H, m). m/e (ES+) 323 (M+H)$^+$.

cis isomer: $\delta_H$ (250 MHz, CDCl$_3$) 1.33–1.36 (3H, m), 1.45 (9H, s), 1.64 (2H, m), 2.47 (1H, m), 2.58–2.94 (2H, m), 3.98–4.08 (1H, m), 4.34 (1H, m 4.77 (1H, m), 7.23–7.30 (1H, m), 7.33–7.35 (4H, m). m/e (ES+) 323 (M+H)$^+$.

Step 2 trans-3-Fluoro-4-[(1R)-1-phenylethylamino]piperidine

Using a similar procedure to that described in Example 1, step 4, trans-1-tert-butoxycarbonyl-3-fluoro-4-[(1R)-1-phenylethylamino]piperidine (0.1147 g, 0.356 mmol) was reacted with trifluoroacetic acid (0.5 mL) in dichloromethane (1.0 mL) to give 75.6 mg (96%) of the title compound as a colourless oil. $\delta_H$ (250 MHz, CDCl$_3$) 1.19 (1H, m), 1.35 (3H, d, J=6.6 Hz), 1.68 (1H, m), 2.40–2.73 (3H, m), 2.85 (1H, m), 3.26 (1H, m), 3.99 (1H, q, J=6.6 Hz), 4.28 (1H, two m, J=49.8 Hz), 7.20–7.35 (5H, m).

Step 3 trans-3-Fluoro-4-[(1R)-phenylethylamino]-1-{3-[5-(1,2,4-triazol-4-yl)-1H-indol-3-yl]propyl}piperidine, oxalate salt Using a similar procedure to that described in Example 1, step 5, 3-[5-(1,2,4-triazol-4-yl)-1H-indol-3-yl]propan-1-ol (0.0529 g, 0.218 mmol) was reacted with methanesulphonyl chloride (34.5 µL, 0.437 mmol) and triethylamine (60.9 µL, 0.437 mmol) in tetrahydrofuran (8 mL), followed by trans-3-fluoro-4-[(1R)-1-phenylethylamino]piperidine (0.0717 g, 0.323 mmol) and potassium carbonate (0.0604 g, 0.437 mmol) in 2-propanol (8 mL). Purification by flash chromatography (silica gel, CH$_2$Cl$_2$—MeOH—NH$_3$ (aq); 94:6:0.6; then alumina, CH$_2$Cl$_2$—MeOH—NH$_3$ (aq); 98:2:0.2) gave 0.0338 g (35%) of the title compound, free base as a colourless solid. The oxalate salt was prepared in MeOH—Et$_2$O; mp 135°–140° C. Found: C, 55.77; H, 5.79; N, 13.02%. C$_{26}$H$_{31}$FN$_6$. 2C$_2$H$_2$O$_4$. 1.1H$_2$O requires C, 55.74; H, 5.80; N, 13.00%. $\delta_H$ (360 MHz, d$_6$-DMSO) 1.40 (3H, d, J=6.3 Hz), 1.57 (1H, m), 1.92 (3H, m), 2.58–2.74 (6H, m), 2.84 (1H, m), 2.97 (1H, in), 3.40 (1H, m), 4.10 (1H, m), 4.79 (1H, two m), 7.29–7.32 (3H, m), 7.36–7.50 (5H, m), 7.77 (1H, s), 9.01 (2H, s), 11.13 (1H, s). m/e (ES+) 447 (M+H)$^+$. The ratio of diastereomers was estimated to be 94:6 by LC/MS.

EXAMPLE 4 trans-3-Fluoro-1-{3-[5-(1,2,4-triazol-4-yl)-1H-indol-3-yl]propyl}-4-[2-(trifluoromethyl)benzylamino]piperidine, oxalate salt Step 1 cis and trans-1-tert-Butoxycarbonyl-3-fluoro-4-[2-(trifluoromethyl)benzylamino]piperidine To a stirred solution of 1-tert-butoxycarbonyl-3-fluoro-4-piperidone (1.0083 g, 4.64 mmol) in anhydrous methanol (20 mL) under argon was added 2-(trifluoromethyl)benzylamine (0.78 mL, 5.56 mmol) and glacial acetic acid (1.06 mL, 18.5 mmol) and the mixture was stirred at room temperature for 1 h before adding sodium cyanoborohydride (0.3540 g, 5.63 mmol) and anhydrous methanol (4 mL). The mixture was stirred at room temperature for a further 4.25 h, then quenched with saturated $K_2CO_3$ (50 mL). The mixture was extracted with ethyl acetate (2×100 mL) and the combined organic extracts were dried ($Na_2SO_4$) and evaporated in vacuo. The residue was purified by flash chromatography (silica gel, 30–40% EtOAc/petroleum ether; and alumina, 20% EtOAc/petroleum ether) to give 0.4670 g (27%) of the trans isomer and 0.5703 g (33%) of the cis isomer of the title compound as colourless oils.

trans isomer: $\delta_H$ (360 MHz, $CDCl_3$) 1.38 (1H, m), 1.46 (9H, s), 1.99 (1H, m), 2.82–2.95 (3H, m), 3.93 (1H, m), 4.02 (2H, s), 4.17–4.44 (2H, m), 7.36 (1H, t, J=7.6 Hz), 7.54 (1H, t, J=7.1 Hz), 7.65 (2H, d, J=8.4 Hz). m/e (ES+) 377 $(M+H)^+$, 321 $(M-CMe_3+2H)^+$.

cis isomer: $\delta_H$ (360 MHz, $CDCl_3$) 1.46 (9H, s), 1.68 (1H, m), 1.80 (1H, m), 2.74 (1H, m), 2.80 (1H, m), 3.00 (1H, m), 4.02 (2H, s), 4.12 (1H, m), 4.33 (1H, m), 4.76 (1H, m), 7.35 (1H, t, J=7.6 Hz), 7.54 (1H, t. J=7.6 Hz), 7.63 (1H, d, J=7.9 Hz), 7.74 (1H, d, J=7.5 Hz). m/e (ES+) 377 $(M+H)^+$, 321 $(M-CMe_3+2H)^+$.

Step 2 trans-3-Fluoro-4-[2-(trifluoromethyl)benzylamino]piperidine

Using a similar procedure to that described in Example 1, step 4, trans-1-tert-butoxycarbonyl-3-fluoro-4-[2-(trifluoromethyl)benzylamino]piperidine (0.4615 g, 1.23 mmol) was reacted with trifluoroacetic acid (1.5 mL) in dichloromethane (3 mL) to give 0.3292 g (97%) of the title compound as a colourless oil. $\delta_H$ (360 MHz, $CDCl_3$) 1.35 (1H, m), 2.02 (1H, m), 2.55–2.69 (2H, m), 2.82 (1H, m), 2.99 (1H, m), 3.31 (1H, m), 4.02 (2H, m), 4.34 (1H, two m), 7.35 (1H, t, J=7.6 Hz), 7.53 (1H, t, J=7.6 Hz), 7.63–7.67 (2H, m). m/e (ES+) 277 $(M+H)^+$.

Step 3 trans-3-Fluoro-1-3-[5-(1,2,4-triazol-4-yl)-1H-indol-3-yl]propyl}-4-[2-(trifluoromethyl)benzylamino]piperidine, oxalate salt Using a similar procedure to that described in Example 1, step 5, 3-[5-(1,2,4-triazol-4-yl)-1H-indol-3-yl]propan-1-ol (0.1906 g, 0.787 mmol) was reacted with methanesulphonyl chloride (0.124 mL, 1.57 mmol) and triethylamine (0.218 mL, 1.56 mmol) in tetrahydrofuran (25 mL), followed by trans-3-fluoro-4-[2-(trifluoromethyl)benzylamino]piperidine (0.3245 g, 1.17 mmol) and potassium carbonate (0.2169 g, 1.57 mmol) in 2-propanol (25 mL). Purification by flash chromatography (alumina, $CH_2Cl_2$—MeOH—$NH_3$ (aq); 98:2:0.2; then silica gel, $CH_2Cl_2$—MeOH—$NH_3$ (aq); 94:6:0.6) gave 0.1622 g (41%) of the title compound, free base. The oxalate salt was prepared in MeOH—$Et_2O$; mp 127°–129° C. Found: C, 54.36; H, 5.11; N, 12.88. $C_{26}H_{28}F_4N_6$. 1.6$C_2H_2O_4$ requires: C, 54.41; H, 4.88; N, 13.04%. $\delta_H$ (360 MHz, $d_6$-DMSO) 1.64 (1H, m), 2.00 (3H, m), 2.58–2.88 (7H, m), 3.10 (1H, m), 3.39 (1H, m), 3.99 (2H, s), 4.71 (1H, two m), 7.30–7.33 (2H, m), 7.49–7.51 (2H, m), 7.68–7.71 (2H, m), 7.79–7.83 (2H, m), 9.01 (2H, s), 11.15 (1H, s). m/e (ES+) 501 $(M+H)^+$.

EXAMPLE 5 trans-3-Fluoro-4-{N-methyl-N-[2-(trifluoromethyl)benzyl]amino}-1-{3-[5-(1,2,4-triazol-4-yl)-1H-indol-3-yl[propyl}piperidine, oxalate salt Using a similar procedure to that described in Example 2, trans-3-fluoro-1-{3-[5-(1,2,4-triazol-4-yl)-1H-indol-3-yl]propyl}-4-[2-(trifluoromethyl)benzylamino]piperidine (98.6 mg, 0.197 mmol) was reacted with 37% wt. solution of formaldehyde (17.7 µL, 0.236 mmol), sodium cyanoborohydride (15.6 mg, 0.248 mmol) and acetic acid (45.1 µL, 0.788 mmol) in methanol (3 mL). Purification by flash chromatography (silica gel, $CH_2Cl_2$—MeOH—$NH_3$ (aq); 95:5:0.5) gave 92.3 mg (91%) of the title compound, free base. The oxalate salt was prepared in MeOH—$Et_2O$; mp 80°–96° C. Found: C, 55.60; H, 5.39; N, 12.40. $C_{27}H_{30}F_4N_6$. 1.5$C_2H_2O_4$. 0.3$C_4H_{10}O$ requires: C, 55.78; H, 5.40; N, 12.51%. $\delta_H$ (360 MHz, $d_6$-DMSO) 1.76 (1H, m), 1.88–2.00 (3H, m), 2.21 (3H, s), 2.58–2.84 (7H, m), 3.18 (1H, m), 3.52 (1H, m), 3.94 (2H, s), 4.89 (1H, two m), 7.30–7.32 (2H, m), 7.45 (1H, t, J=8.0 Hz), 7.49 (1H, d, J=8.6 Hz), 7.64–7.69 (2H, m), 7.80–7.83 (2H, m), 9.01 (2H, s), 11.13 (1H, s). m/e (ES+) 515 $(M+H)^+$.

EXAMPLE 6 cis-3-Fluoro-1-{3-[5-(1,2,4-triazol-4-yl)-1H-indol-3-yl]propyl}-4-[2-(trifluoromethyl)benzylamino]piperidine, oxalate salt Step 1 cis-3-Fluoro-4-[2-(trifluoromethyl)benzylamino]piperidine Using a similar procedure to that described in Example 1, step 4, cis-i-tert-butoxycarbonyl-3-fluoro-4-[2-(trifluoromethyl)benzylamino]piperidine (0.5646 g, 1.50 mmol) was reacted with trifluoroacetic acid (1.5 mL) in dichloromethane (3 mL) to give 0.3998 g (97%) of the title compound as a colourless oil. $\delta_H$ (360 MHz, $CDCl_3$) 1.56 (1H, m), 1.83 (1H, m), 2.56–2.79 (3H, m), 3.12 (1H, m), 3.34 (1H, m), 4.03 (2H, s), 4.73 (1H, d, J=49.1 Hz), 7.35 (lH, t, J=7.7 Hz), 7.54 (1H, t, J=7.7 Hz), 7.63 (1H, d, J=7.7 Hz), 7.76 (1H, d, J=7.6 Hz). m/e (ES+) 277 $(M+H)^+$.

Step 2 cis-3-Fluoro-1-{3-[5-(1,2,4-triazol-4-yl)-1H-indol-3-yl]propyl}-4-[2-(trifluoromethyl)benzylamino]piperidine, oxalate salt Using a similar procedure to that described in Example 1, step 5, 3-[5-(1,2,4-triazol-4-yl)-1H-indol-3-yl]propan-1-ol (0.2312 g, 0.954 mmol) was reacted with methanesulphonyl chloride (0.151 mL, 1.91 mmol) and triethylamine (0.266 mL, 1.91 mmol) in tetrahydrofuran (30 mL), followed by cis-3-fluoro-4-[2-(trifluoromethyl)benzylamino]piperidine (0.3950 g, 1.43 mmol) and potassium carbonate (0.2642 g, 1.91 mmol) in 2-propanol (30 mL). Purification by flash chromatography (alumina, $CH_2Cl_2$—MeOH—$NH_3$ (aq); 98:2:0.2; then silica gel, $CH_2Cl_2$—MeOH—$NH_3$ (aq); 94:6:0.6) gave 0.2096 g (44%) of the title compound, free base. The oxalate salt was prepared in MeOH—$Et_2O$; mp 116°–120° C. Found: C, 52.70; H, 5.09; N, 12.22. $Cl_{26}H_{28}F_4N_6$. 2$C_2H_2O_4$ requires: C, 52.94; H, 4.74; N, 12.35%. $\delta_H$ (360 MHz, $d_6$-DMSO) 1.81 (1H, m), 1.92–2.03 (3H, m), 2.69–3.12 (7H, m), 3.30 (1H, m), 3.60 (1H, m), 3.99 (2H, s), 5.04 (1H, d, J=46.4 Hz), 7.31–7.33 (2H, m), 7.48–7.51 (2H, m), 7.66–7.71 (2H, m), 7.79 (1H, s), 7.84 (1H, d, J=7.4 Hz), 9.01 (2H, s), 11.17 (1H, s). m/e (ES+) 501 $(M+H)^+$.

EXAMPLE 7 cis-3-Fluoro-4-{N-methyl-N-[2-(trifluoromethyl)benzyl]amino}-1-{3-[5-(1,2,4-triazol-4-yl)-1H-indol-3-yl]propyl}piperidine, oxalate salt Using a similar procedure to that described in Example 2, cis-3-fluoro-1-{3-[5-(1,2,4-triazol-4-yl)-1H-indol-3-yl]

propyl}-4-[2-(trifluoromethyl)benzylamino]piperidine (0.1419 g, 0.283 mmol) was reacted with 37% wt. solution of formaldehyde (25.5 μL, 0.340 mmol), sodium cyanoborohydride (21.2 mg, 0.337 mmol) and acetic acid (64.9 μL, 1.13 mmol) in methanol (4 mL). Purification by flash chromatography (silica gel, $CH_2Cl_2$—MeOH—$NH_3$ (aq); 95:5:0.5) gave 0.1336 g (92%) of the title compound, free base. The oxalate salt was prepared in MeOH—$Et_2O$; mp 95°–97° C. Found: C, 54.92; H, 5.27; N, 12.27. $C_{27}H_{30}F_4N_6$. $1.7C_2H_2O_4$ requires: C, 54.69; H, 5.04; N, 12.59%. $\delta_H$ (360 MHz, $d_6$-DMSO) 1.89 (1H, m), 1.98–2.10 (3H, m), 2.22 (3H, s), 2.76–3.10 (7H, m), 3.42 (1H, m), 3.62 (1H, m), 3.83 (2H, m), 5.25 (1H, d, J=48.0 Hz), 7.31–7.33 (2H, m), 7.46 (1H, t, J=7.3 Hz), 7.50 (1H, d, J=8.6 Hz), 7.64–7.70 (2H, m), 7.80–7.82 (2H, m), 9.01 (2H, s), 11.17 (1H, s). m/e (ES+) 515 (M+H)$^+$.

We claim:

1. A compound of formula I, or a salt or prodrug thereof:

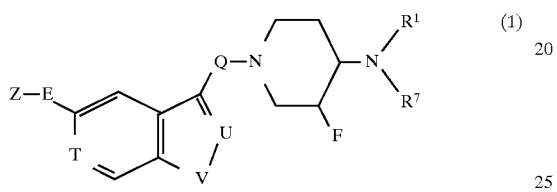
(1)

wherein

Z represents hydrogen halogen, cyano, nitro, trifluoromethyl, —$OR^5$, —$OCOR^5$, —$OCONR^5R^6$, —$OCH_2CN$, —$OCH_2CONR^5R^6$, —$SR^5$, —$SOR^5$, —$SO_2R^5$, —$SO_2NR^5R^6$, —$NR^5R^6$, —$NR^5COR^6$, —$NR^5CO_2R^6$, —$NR^5SO_2R^6$, —$COR^5$, —$CO_2R^5$, —$CONR^5R^6$, or a group of formula (Za), (Zb), (Zc) or (Zd):

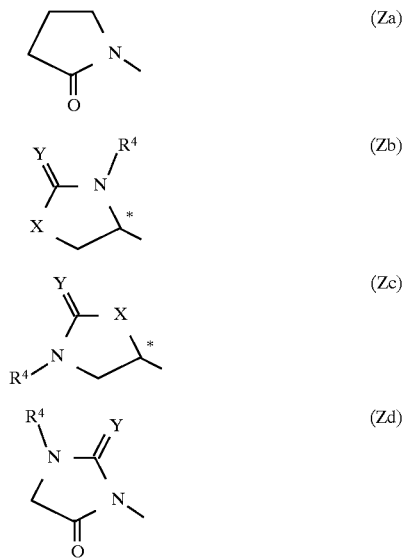

in which the asterisk * denotes a chiral center; or

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole wherein the optional substituents are selected from $C_{1-6}$ alkyl, $C_{2-6}$ alkylenyl, $C_{2-6}$ alkynyl, $C_{3-7}$ cycloalkyl, aryl, aryl ($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano and trifluoromethyl; or Z represents an optionally substituted six-membered heteroaromatic ring selected from pyridine, pyrazine, pyrimidine and pyridazine wherein the optional substituents are selected from $C_{1-6}$ alkyl, $C_{2-6}$ alkyenyl, $C_{2-6}$ alkyenyl, $C_{2-6}$ alkynyl, $C_{3-7}$ cycloalkyl, aryl, aryl ($C_{1-6}$)alkyl, $C_{3-7}$ heterocycloalkyl, heteroaryl, heteroaryl($C_{1-6}$)alkyl, halogen, halo $C_{1-6}$ alkyl, cyano, cyano $C_{1-6}$ alkyl, trifluoromethyl and —$(CH_2)_a$—$R^8$, in which a is zero, 1, 2 or 3 (preferably zero or 1) and $R^8$ represents —$OR^a$, —$OCOR^c$, —$OCO_2R^a$, —$SR^a$, —$SOR^a$, —$SO_2R^c$, —CH=$CHSO_2R^c$, —$SO_2NR^aR^b$, —CH=$CHSO_2NR^aR^b$, —$NR^aR^b$, —$NR^aCOR^c$, —$NR^aCO(CH_2)_bORd$ (in which b is 1 or 2, preferably 1), —$NR^aCO_2R^d$, —$NR^aSO_2R^c$, —$NR^dCONR^aR^b$, —$NR^dSO_2NR^aR^b$, —$COR^c$, —CH=$CHCOR^c$, —$CO_2R^a$, —$CONR^aR^b$, —CH=$CHCONR^aR^b$, or $CONR^dNR^aR^b$, or $R^8$ represents a group of formula (a), (b), (c), (d) or e);

(a)

(b)

(c)

(d)

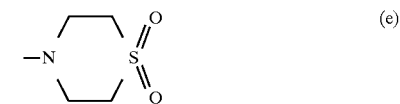
(e)

wherein $R^a$ and $R^d$ independently represent hydrogen, $C_{1-6}$ alkyl, trifluoromethyl, phenyl, fluorophenyl or tetrahydropyranyl; $R^b$ represents hydrogen,, $C_{1-6}$ alkyl, trifluoromethyl, phenyl or fluorophenyl; and $R_c$ represents hydrogen, $C_{1-6}$ alkyl, trifluoromethyl, phenyl, fluorophenyl, tetrahydropyranyl, azetidinyl, pyrrolidinyl, piperidinyl or morpholinyl;

X represents oxygen, sulphur, —NH— or methylene;

Y represents oxygen or sulphur;

E represents a chemical bond or a straight or branched alkylene chain containing from 1 to 4 carbon atoms;

Q represents a straight or branched alkylene chain containing from 1 to 6 carbon atoms, optionally substituted in any position by one or more substituents selected from fluoro and hydroxy;

T represents nitrogen or CH;

U represents nitrogen or C—$R^2$;

V represents oxygen, sulphur or N—$R^3$;

$R^1$ represents aryl($C_{1-6}$)alkyl or heteroaryl($C_{1-6}$)alkyl, either of which groups may be optionally substituted;

$R^2$, $R^3$, $R^4$ and $R^7$ independently represent hydrogen or $C_{1-6}$ alkyl; and $R^5$ and $R^6$ independently represent hydrogen, $C_{1-6}$ alkyl, trifluoromethyl, phenyl methylphenyl, or an optionally substituted aryl($C_{1-6}$)alkyl or heteroaryl($C_{1-6}$)alkyl group; or $R^5$ and $R^6$, when linked through a nitrogen atom, together represent the residue of an optionally substituted azetidine, pyrrolidine, piperidine, morpholine or piperazine ring wherein the optional substituents are selected from methyl, benzyl, methoxy, methoxycarbonyl, ethoxycarbonyl and methylaminocarbonyl;

and wherein in the foregoing, "aryl" includes phenyl and naphthyl; "heterocycloalkyl" includes azetidinyl, pyrrolidinyl, piperidinyl, piperazinyl and morpholinyl; and heteroaryl includes pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl indazolyl, oxazolyl, isoxazolyl, thiazolyl, isothiazolyl, imidazolyl, benzimidazolyl, oxadiazolyl, thiadiazolyl, triazolyl and tetrazolyl.

2. A compound as claimed in claim 1 represented by formula ID:

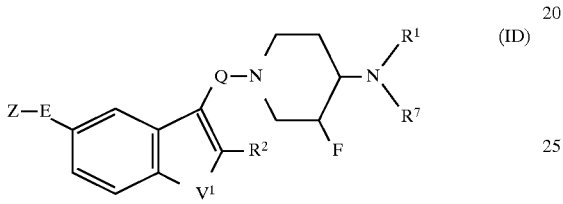

wherein $V^1$ represents oxygen or N—$R^3$, and Z, E, Q, $R^1$, $R^2$, $R^3$ and $R^7$ are as defined in claim 1.

3. A compound as claimed in claim 1 wherein Z represents an unsubstituted or substituted imidazol-1-yl, 1,2,4-triazol-1-yl or 1,2,4-triazol-4-yl moiety.

4. A compound as claimed in claim 3 wherein Z represents a 1,2,4-triazol-4-yl moiety.

5. A compound as claimed in claim 1 wherein E represents a chemical bond or a methylene linkage.

6. A compound as claimed in claim 5 wherein E represents a chemical bond.

7. A compound as claimed in claim 1 wherein Q represents a propylene linkage.

8. A compound as claimed in claim 1 wherein $R^1$ represents benzyl, trifluoromethyl-benzyl or 1-phenylethyl.

9. A compound as claimed in claim 1 wherein $R^7$ represents hydrogen or methyl.

10. A compound as claimed in claim 1 represented by formula IIA, and salts and prodrugs thereof:

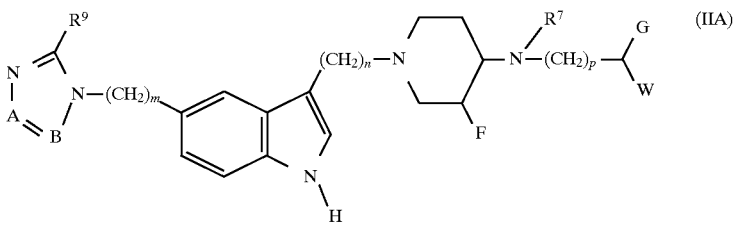

wherein
m is zero, 1, 2 or 3;
n is 2, 3 or 4;
p is zero, 1 or 2;
A represents nitrogen or CH;
B represents nitrogen or C—$R^{10}$;
$R^7$ is as defined in claim 1;
$R^9$ and $R^{10}$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl;

G represents hydrogen, $C_{1-3}$ alkyl or hydroxy($C_{1-3}$)alkyl; and

W represents a group of formula (Wa), (Wb) or (Wc):

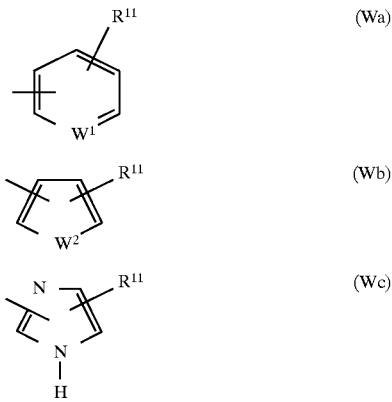

in which
$W^1$ represents CH or nitrogen;
$W^2$ represents oxygen, sulphur, NH or N-methyl; and
$R^{11}$ represents hydrogen, halogen, cyano, trifluoromethyl, triazolyl, tetrazolyl, $C_{1-6}$ alkyl-tetrazolyl, $C_{1-6}$ alkoxy, $C_{2-6}$ alkylcarbonyl, amino, $C_{1-6}$ alkylamino, di($C_{1-6}$) alkylamino, di($C_{1-6}$)alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl or $C_{1-6}$ alkylaminosulphonylmethyl.

11. A compound as claimed in claim 10 wherein $R^9$ and $R^{10}$ represent hydrogen.

12. A compound as claimed in claim 10 wherein $R^{11}$ represents hydrogen or trifluoromethyl.

13. A compound as claimed in claim 10 wherein G represents hydrogen or methyl.

14. A compound as claimed in claim 10 wherein W represents a group of formula (Wa).

15. A compound as claimed in claim 14 wherein $W^1$ represents CH.

16. A compound selected from:
cis-4-benzylamino-3-fluoro-1-{3-[5-(1,2,4-triazol-4-yl)-1H-indol-3-yl]propyl}piperidine;
cis-4-(N-benzyl-N-methylamino)-3-fluoro-1-{3-[5-(1,2,4-triazol-4-yl)-1H-indol-3-yl]propyl}piperidine;
trans-3-fluoro-4-[(1R)-1-phenylethylamino]-1-{3-[5-(1,2,4-triazol-4-yl)-1H-indol-3-yl]propyl}piperidine;
trans-3-fluoro-1-{3-[5-(1,2,4-triazol-4-yl)-1H-indol-3-yl]propyl}-4-[2-(trifluoromethyl)benzylamino]piperidine;
trans-3-fluoro-4-{N-methyl-N-[2-(trifluoromethyl)benzyl]amino}-1-{3-[5-(1,2,4-triazol-4-yl)-1H-indol-3-yl]propyl}piperidine;

cis-3-fluoro-1-{3-[5-(1,2,4-triazol-4-yl)-1H-indol-3-yl]propyl}-4-[2-(trifluoromethyl)benzylamino]piperidine;

cis-3-fluoro-4-{N-methyl-N-[2-(trifluoromethyl)benzyl]amino}-1-{3-[5-(1,2,4-triazol-4-yl)-1H-indol-3-yl]propyl}piperidine;

and salts and prodrugs thereof.

17. A pharmaceutical composition comprising an effective amount of a compound of formula I as defined in claim 1 or a pharmaceutically acceptable salt thereof or a prodrug thereof in association with a pharmaceutically acceptable carrier.

18. A method for the treatment and/or prevention of migraine or headache for which an agonist of 5-$HT_{1D}$ receptors selective for the 5-$HT_{1D_\alpha}$ subtype thereof is indicated, which method comprises administering to a patient in need of such treatment a 5$HT_{1D_\alpha}$ agonistic effective amount of a compound of formula I as defined in claim 1 or a pharmaceutically acceptable salt thereof or a prodrug thereof.

* * * * *

UNITED STATES PATENT AND TRADEMARK OFFICE
CERTIFICATE OF CORRECTION

PATENT NO. : 5,837,715

DATED : November 17, 1998

INVENTOR(S) : J. L. Castro Pineiro and M. G. Russell

It is certified that error appears in the above-identified patent and that said Letters Patent is hereby corrected as shown below:

ON THE TITLE PAGE, ADD:

[30]   Foreign Application Priority Data

Jul. 25, 1996   [GB]   United Kingdom ..........9615658

Signed and Sealed this

Eighteenth Day of May, 1999

Attest:

Q. TODD DICKINSON

*Attesting Officer*   Acting Commissioner of Patents and Trademarks